(12) United States Patent
Hennen

(10) Patent No.: US 9,849,157 B2
(45) Date of Patent: *Dec. 26, 2017

(54) CARDIOVASCULAR THERAPY COMPOSITIONS

(75) Inventor: William J. Hennen, Springville, UT (US)

(73) Assignee: 4LIFE PATENTS, LLC, Sandy, UT (US)

( * ) Notice: Subject to any disclaimer, the term of this patent is extended or adjusted under 35 U.S.C. 154(b) by 564 days.

This patent is subject to a terminal disclaimer.

(21) Appl. No.: 12/906,883

(22) Filed: Oct. 18, 2010

(65) Prior Publication Data

US 2011/0033414 A1   Feb. 10, 2011

Related U.S. Application Data

(63) Continuation of application No. 10/646,615, filed on Aug. 22, 2003, now Pat. No. 7,815,943.

(60) Provisional application No. 60/405,358, filed on Aug. 22, 2002.

(51) Int. Cl.
| | | |
|---|---|---|
| *A61K 38/17* | (2006.01) | |
| *A61K 31/22* | (2006.01) | |
| *A61K 31/198* | (2006.01) | |
| *A61K 31/465* | (2006.01) | |
| *A61K 35/20* | (2006.01) | |
| *A61K 35/44* | (2015.01) | |
| *A61K 45/06* | (2006.01) | |

(52) U.S. Cl.
CPC ............ *A61K 38/17* (2013.01); *A61K 31/198* (2013.01); *A61K 31/22* (2013.01); *A61K 31/465* (2013.01); *A61K 35/20* (2013.01); *A61K 35/44* (2013.01); *A61K 38/1709* (2013.01); *A61K 45/06* (2013.01)

(58) Field of Classification Search
CPC .. A61K 2300/00; A61K 31/198; A61K 35/20; A61K 31/465; A61K 38/1709; A61K 31/22; A61K 35/44; A61K 45/06; A61K 38/17
USPC ................ 514/1.9, 7.4; 424/535, 520, 157.1
See application file for complete search history.

(56) References Cited

U.S. PATENT DOCUMENTS

| | | | |
|---|---|---|---|
| 4,816,563 A | 3/1989 | Wilson et al. | |
| 5,080,895 A | 1/1992 | Tokoro | |
| 5,470,835 A | 11/1995 | Kirkpatrick et al. | |
| 5,650,418 A | 7/1997 | Rath et al. | |
| 6,022,901 A | 2/2000 | Goodman | |
| 6,203,818 B1 | 3/2001 | Vester | |
| 6,468,534 B1 | 10/2002 | Hennen et al. | |
| 6,506,413 B1 | 1/2003 | Ramaekers | |
| 6,693,094 B2 | 2/2004 | Pearson et al. | |
| 2002/0044942 A1* | 4/2002 | Dopson | ........................ 424/184.1 |

OTHER PUBLICATIONS

Leinonen and Saikku.Evidence for infectious agents in cardiovascular disease and atherosclerosis. Lancet Infectious Diseases 2002; 2: 11-17.*
Cholesterol-lowering drugs (http://www.americanheart.org/presenter;jhtml?identifier=4510; p. 2).
Focant et al., The Effect of Vitamin E. Supplementation of Cow Diets Containing Rapeseed and Linseed on the Prevention of Milk Fat Oxidation, J. Dairy Sci., 1998, 81:1095-1101, Abstract.
Tentolouris et al., L-Arginine in coronary atherosclerosis, Int. J. Cardiol., 2000, 75(2-3):123-128.
Gordon Cardovascular Research. Explore, 1999, http://www.explorepub.com/articles/heart_disease.html, p. 3.
Kirkpatrick Properties and activities of transfer factor, J. Allergy and Clin. Immunol. 1975, 55(6):411-421; Abstract.
Vercellotti. Microbes, inflammation and atherosclerosis: will old pathology lessons guide new therapies? Trans Am Clin. Climatol. Assoc. 2001, 112:215-222, Abstract.
Singh et al., Coenzyme Q in cardiovascular disease, J. Assoc. Physicians India; Mar. 1998; 46(3):299-306; Abstract.
Campbell et al., 1998, Chlamydia pneumoniae and Cardiovascular Disease, Emerging Infectious Diseases, vol. 4, No. 4, Oct.-Dec., p. 571-579.
Kemper, 1999, Ginger (*Zingiber officinale*), Longwood Herbal Task Force: http://www.mcp.edu/herbal/default.htm, p. 1-18.
Szapary et al., 2000, Alternative Medicine in Cardiovascular Disease: More Questions Than Answers, ACC Current Journal Review, p. 104-108.
Williamson et al., 1997, Herbal therapies: The facts and the fiction, Drug Topics, p. 78-87.
PCT International Search Report dated Mar. 19, 2004, performed for application PCT/US03/26427.
U.S. Appl. No. 60/423,965, filed Nov. 4, 2002, and entitled "Methods and Compositions for Focusing Cell-Mediated Immune Response and Enhancing Efficiency of an Individual's Antioxidant Profile Detoxification Abilities, and General Cell and Molecular Health".

* cited by examiner

*Primary Examiner* — Taeyoon Kim
(74) *Attorney, Agent, or Firm* — Durham Jones & Pinegar, P.C. Intellectual Property Law Group

(57) ABSTRACT

A composition for use in cardiovascular therapy includes transfer factor. The transfer factor may be nonmammalian transfer factor, such as that derived from eggs, or mammalian transfer factor, such as that derived from colostrum. The composition may also include one or more of the following: an LDL receptor-binding element; a blood flow-enhancing element; a cholesterol reducing element; a fat oxidation prevention element, and an antioxidant. Treatment methods include enlisting the immune system of a subject receiving therapy to attack pathogens that cause inflammation of blood vessels or to otherwise reduce inflammation of blood vessels.

35 Claims, No Drawings

CARDIOVASCULAR THERAPY COMPOSITIONS

CROSS-REFERENCE TO RELATED APPLICATION

This application is a continuation of U.S. patent application Ser. No. 10/646,813 filed Aug. 22, 2003 entitled CARDIOVASCULAR THERAPY COMPOSITION INCLUDING TRANSFER FACTOR AND THERAPEUTIC METHODS INCLUDING USE OF THE COMPOSITION, which claims priority under the provisions of 35 U.S.C. §119(e), from U.S. Provisional Patent Application Ser. No. 60/405,358, filed on Aug. 22, 2002, the disclosures of which are hereby incorporated by reference in their entirety by this reference as if set forth herein.

BACKGROUND OF THE INVENTION

Field of the Invention

The present invention relates generally to compositions, including nutritional supplements, for use in improving cardiovascular health and, more specifically, to compositions that may be useful for preventing arteriosclerosis.

Background of Related Art

The term "cardiovascular disease," as used herein, is intended to refer to all pathological states leading to a narrowing and/or occlusion of blood vessels throughout the body. In particular, the term "cardiovascular disease" refers to conditions including atherosclerosis, thrombosis and other related pathological states, especially within arteries of the heart and brain. Accordingly, the term "cardiovascular disease" encompasses, without limitation, various types of heart disease, as well as Alzheimer's disease and vascular dimension.

For some time, conventional medical treatment of cardiovascular disease has focused on low density lipoprotein, or "LDL," the so called "bad cholesterol," and strategies for lowering its concentration in the bloodstream. A great many studies have been published ostensibly linking cardiovascular disease with elevated levels of LDL. As a result, most therapies for the prevention and treatment of cardiovascular disease rely on drugs that reduce serum levels of LDL in the bloodstream. More recent studies have found the effects of lowering LDL levels on cardiovascular disease to be somewhat equivocal. Thus, the efficacy of LDL-reducing drugs and therapies continues to be a source of major debate within the medical community.

Lipoprotein(a) ("Lp(a)") binds LDL receptors on the walls of blood vessels. Lp(a) also binds lysine-sepharose, immobilized fibrin and fibrinogen, and the plasminogen receptor on endothelial cells. Additionally, Lp(a) binds other components of the arterial wall, including fibrinectin and glycosaminoglycans. High levels of Lp(a) in blood are known to be associated with the incidence of cardiovascular disease, likely due to the cross-linking effects of Lp(a) that has bound to LDL receptors on blood vessel walls.

Some cardiovascular therapies are designed to reduce the binding of Lp(a) by LDL receptors that are present on the interior walls of the arteries and include antioxidants to reduce swelling of the arteries. By way of example, U.S. Pat. No. 5,650,418 to Rath et al. (hereinafter "Rath") describes a cardiovascular disease treatment composition which includes lysine or a pharmaceutically acceptable salt thereof, nicotinic acid, and ascorbic acid (i.e., vitamin C). The lysine binds LDL receptors and, thus, prevents Lp(a) from binding such receptors, thereby reducing the negative affects of Lp(a) on the arteries. Nicotinic acid and ascorbic acid are antioxidants, which reduce swelling of the arterial walls, thereby permitting more blood to flow through the arteries and, to some extent, reducing blood pressure.

In addition to high levels of Lp(a), it is believed that several pathogens, including herpes simplex virus-2 (HSV-2), may be partially responsible for causing cardiovascular disease. Among other things, it is believed that such pathogens cause swelling of the arterial walls, which results in vasoconstriction. In turn, vasoconstriction restricts the flow rate of blood through the arteries and increases blood pressure.

Also, it is believed that such pathogens may damage the walls of blood vessels, which results in the binding of Lp(a) thereto.

While the composition described in Rath reduces the effects of Lp(a) and reduces some swelling of the arteries, it does not target the causes of such swelling to eliminate the same.

The inventor is not aware of a composition for use in cardiovascular therapy that includes one or more components that target the pathogenic causes of swelling of the arteries and enlist the immune system of a subject (e.g., a mammal, such as a human or any other mammal) to reduce or eliminate such pathogenic causes of such inflammation, which may contribute to cardiovascular disease.

SUMMARY OF THE INVENTION

The present invention includes compositions for use in cardiovascular therapy and which may be useful for preventing or treating cardiovascular disease, as well as cardiovascular therapy methods.

Compositions that incorporate teachings of the present invention include, among other things, a component of mammalian, avian, and other immune systems known as "transfer factor." The transfer factor used in the composition may be either an antigen-nonspecific or pathogen-nonspecific transfer factor or one or more transfer factors which have specificity for one or more pathogens or antigens thereof.

Other components that may be included in compositions of the present invention include, but are not limited to, LDL receptor-binding elements, blood flow-enhancing elements, blood cholesterol reducers, fat oxidation prevention elements, and antioxidants. A composition that incorporates teachings of the present invention may include any combination of the foregoing elements and one or more of each such element.

Treatment methods include administration of the composition to a subject either enterally or parenterally, in a known fashion. Due to the presence of transfer factor in the composition, the composition enlists the immune system of a treated subject against pathogens that may cause inflammation or lesions that may lead to cardiovascular disease. Other components of such a composition may act to prevent Lp(a) from binding to LDL receptors on the walls of blood vessels, prevent and/or repair damage to the blood vessels, reduce inflammation, improve blood flow, reduce blood cholesterol levels, and/or prevent fats from oxidizing and, thus, from sticking to the walls of blood vessels.

Other features and advantages of the present invention will become apparent to those of skill in the art through consideration of the ensuing description and the appended claims.

DETAILED DESCRIPTION

Compositions that incorporate teachings of the present invention include transfer factor or other inflammation-reducing or pathogen-reducing components and are useful in cardiovascular therapy and, more particularly, in preventing or even reducing cardiovascular disease, including atherosclerosis and other disease states that may result therefrom, as well as for improving the overall cardiovascular efficiency of a subject. Cardiovascular therapy methods that employ such compositions are also within the scope of the present invention.

In addition to transfer factor, an exemplary embodiment of a composition according to the present invention includes an LDL receptor-binding element, a blood flow-enhancing element, a blood cholesterol reducer, and at least one antioxidant.

The transfer factor of a composition according to the present invention may comprise an antigen-nonspecific or pathogen-nonspecific transfer factor, an antigen-specific or pathogen-specific transfer factor, or a combination of non-specific and specific transfer factor molecules. If an antigen-specific or pathogen-specific transfer factor is used, the transfer factor may have specificity for pathogenic agents which may cause cardiovascular complications or otherwise affect the circulatory system, such as by causing the arterial walls to swell. For example, the composition may include transfer factor which has specificity for one or more of the herpes simplex viruses-1 and -2 (respectively, "HSV-1"and "HSV-2"), *Chlamydia pneumoniae*, cytomegalovirus ("CMV"), *Helicobacter pylori*, and various oral pathogens.

Also, the transfer factor may comprise a nonmammalian transfer factor, such as egg-derived avian transfer factor or blood-derived transfer factor (e.g., transfer factor from chicken blood) or a mammalian transfer factor, such as colostrum-derived transfer factor, spleen-derived transfer factor, or blood-derived transfer factor. U.S. Pat. No. 6,468,534 to Hennen et al., the disclosure of which is hereby incorporated herein in its entirety by this reference, describes egg-derived transfer factor as well as processes for obtaining the same. Colostrum-derived transfer factor and exemplary processes for obtaining the same are described in U.S. Pat. No. 4,816,563 to Wilson et al., the disclosure of which is hereby incorporated herein in its entirety by this reference. Compositions which include combinations of different types of transfer factor molules, or transfer factor molecules from different sources, are also within the scope of the present invention.

The transfer factor in a composition incorporating teachings of the present invention enlists the immune system of a subject who receives cardiovascular therapy or is being treated with such a composition against pathogens, including viruses, bacteria, and other pathogenic agents, that may contribute to cardiovascular disease, including atherosclerosis. In enlisting the immune system of a subject in this manner, the transfer factor causes the immune system to reduce inflammation, as is well known in the art, and may cause the immune system to reduce or eliminate the number of such pathogens in the body of the subject.

The TEST EXAMPLE that follows provides data that shows the degree to which transfer factor causes an increase in the activity of natural killer cells, which are also referred to in the art as "cytotoxic T-lymphocytes" ("CTLs"), in attacking pathogens. The tests conducted were chromium-51 (radioactive chromium, or 51 Cr) assays. The tests were conducted in vitro on cell cultures, including *C. pneumoniae* and *H. pylori* bacterial cells and HSV-1-infected and HSV-2-infected mammalian cell lines. In the control, a fixed amount of natural killer cells was introduced into the cellular milieu along with a fixed amount of flour for a period of four hours, then the amount of chromium-51 that had been released was analyzed with a Beckman 2000 gamma counter. In a first set of test samples, the same, fixed amount of natural killer cells was introduced into the cellular milieu along with a composition including bovine transfer factor in an amount equal to the amount of flour introduced into the control. A second set of test samples included the fixed amount of natural killer cells, as well as a composition including avian transfer factor in an amount equal to the amounts of flour in the control samples and the bovine transfer factor-containing composition in the first set of samples. The results follow:

| TEST EXAMPLE | | | | |
|---|---|---|---|---|
| Pathogen Additive | *C. pneumoniae* | *H. pylori* | HSV-1 | HSV-2 |
| | chromium-51 counts per minute (cpm): | | | |
| Flour | 1323 | 1121 | 2017 | 1262 |
| Bovine TF | 2593 | 2499 | 2240 | 2473 |
| percent increase | 196% | 223% | 111% | 196% |
| Avian TF | 2553 | 1860 | 2985 | 2183 |
| percent increase | 193% | 166% | 148% | 173% |

The data shown in the TEST EXAMPLE indicate that both bovine transfer factor and avian transfer factor increase the activity of natural kill cells, reducing levels of *C. pneumoniae*, *H. pylori*, HSV-1 and HSV-2. It follows that the role that each of these pathogens plays in cardiovascular disease would also be reduced or eliminated by therapy with mammalian transfer factor or nonmammalian transfer factor.

The LDL receptor-binding element may, by way of example only, comprise lysine or a lysine-containing compound, such as magnesium lysinate, lysine hydrochloride, lysine dihydrochloride, lysine orotate, lysine succinate, lysine glutamate, or the like.

Since LDL receptor-binding elements are capable of occupying the sites on LDL receptors to which Lp(a) and LDL bind, LDL receptor-binding elements are useful for preventing Lp(a) from binding the LDL receptors and, thus, from additionally binding other components of the arterial walls, which binding is believed to contribute to cardiovascular disease.

Exemplary blood flow-enhancing elements, or vasodilators, that may be included in a composition of the present invention include, without limitation, arginine and arginine-containing compounds, such as magnesium arginate. Other blood flow-enhancing elements, such as niacinamide, may alternatively or additionally be included in such a composition. By way of example only, the blood flow-enhancing elements may target cardiovascular vessels located around the heart or improve blood flow in a more general fashion (i.e., throughout the body of a treated subject). Combinations of blood flow-enhancing elements that have different blood flow-enhancing characteristics may also be used in a composition that incorporates teachings of the present invention.

By increasing the rate at which blood flows through cardiovascular vessels, blood flow-enhancing elements may reduce blood pressure, reduce monocyte adhesion and thereby augment endothelial function, and, as a result, prevent the generation of and even reduce the occurrence of pathophysiological lesions on the walls of cardiovascular vessels.

Blood cholesterol reducers may also be included in a composition according to the present invention. Examples of useful blood cholesterol reducers include, without limitation, nicotinic acid (which is a form of Niacin, or vitamin B$_3$) or any other agent which is known to reduce cholesterol levels in blood. Of course, the utility of a blood cholesterol reducer in a composition according to the present invention is that it will reduce the amount of cholesterol, including LDL, in the blood of a subject, thereby reducing the potential for cholesterol-induced cardiovascular disease.

Antioxidants, including coenzymes, vitamins (e.g., vitamin E, vitamin A, beta-carotene, vitamin C, etc.), and the like are useful for preventing and treating damage to the walls of the arteries, as is well known in the art. In addition, both mammalian and nonmammalian transfer factors are known to increase the antioxidant and detoxification abilities of a treated subject. Data and specific information regarding these abilities of transfer factor are provided in U.S. Provisional Patent Application Ser. No. 60/423,965, filed on Nov. 4, 2002, the disclosure of which is hereby incorporated herein in its entirety by this reference.

A composition according to the present invention may also include vitamin B$_6$, which is available as pyridoxine hydrochloride and pyridoxal-5-phosphate. Vitamin B$_6$ deficiency has long been associated with atherosclerosis. It is well documented that vitamin B$_6$ is useful for treating atherosclerosis, as well as for reducing blood pressure and for facilitating the removal of toxins from the body of a subject.

Of course, a composition of the present invention which is used to treat or prevent the occurrence of cardiovascular disorders may lack some of the foregoing elements, or it may include additional components that are known or believed to improve the cardiovascular health of a subject.

The following is an example of a composition that incorporates teachings of the present invention:

Exemplary Composition

| INGREDIENT | AMOUNT (per capsule) |
| --- | --- |
| Transfer Factor (Cardio-TF-XF ™) | 50 mg |
| Proprietary Blend | 144.5 mg |
| Butcher's Broom (root) (22% sterolic heterosides) | |
| Ginkgo biloba (leaf) (24% ginkgo flavone glycosides), 6% terpene lactones) | |
| Hawthorn (flower and leaf) (1.8% rutin) | |
| Garlic (deodorized clove) | |
| Coenzyme Q$_{10}$ | |
| Red Rice Yeast Extract | |
| Resveratrol (from *Polygonum cuspidatum*) | |
| Ginger Oil | |
| Vitamin A (as beta carotene) | 2,500 IU |
| Vitamin C (as magnesium dehydroascorbate, ascorbyl palmitate, and ascorbic acid) | 50 mg |
| Vitamin E (as d-alpha tocopherol succinate) | 100 IU |
| Niacin (as niacinamide) | 5 mg |
| Vitamin B$_6$ (as pyridoxine hydrochloride) | 0.5 mg |
| Folate (as folic acid) | 100 mcg |
| Vitamin B$_{12}$ (as cyancobalamin) | 2 mcg |
| Magnesium (as magnesium chloride, magnesium dehydroascorbate, magnesium arginate, and magnesium lysinate) | 45 mg |
| Zinc (as zinc arginate) | 2.5 mg |
| Selenium (as selenomethionine) | 12.5 mcg |
| Copper (as copper glycinate) | 0.5 mg |
| Potassium (as potassium citrate) | 12.5 mg |
| TOTAL | 310.6 mg |

The EXEMPLARY COMPOSITION is marketed by 4Life Research, LLC, of Sandy, Utah, as TF CARDIO®. The above-listed ingredients are contained within each capsule of the EXEMPLARY COMPOSITION.

In the EXEMPLARY COMPOSITION, the transfer factor is at least a part of an inflammation-reducing component or pathogen-reducing component and comprises Cardio-TF-XF™, which includes transfer factor specific for HSV-1, HSV-2,*Chlamydia pneumoniae*, CMV, *Helicobacter Pylori*, and other pathogens (e.g., those of the oral cavity) that are known to cause lesions and swelling in arterial walls. By enlisting the immune system of a treated subject in resisting such pathogens, the transfer factor component of a composition incorporating teachings of the present invention reduces a cause of inflammation and lesions that are at least partially responsible for many cardiovascular disorders. The transfer factors of Cardio-TF-XF™ are avian transfer factors which have been derived from the eggs of chickens.

Additionally, transfer factor is known to generally reduce inflammation in a subject, including in blood vessels of the subject, even when pathogens such as those listed above are not present. As is well-known in the art, inflammation, whether pathogen-induced or not, is known to contribute to cardiovascular disease.

The composition of the EXEMPLARY COMPOSITION also includes an LDL receptor-binding element in the form of magnesium lysinate, a lysine salt. As described previously herein, when a form of lysine binds the LDL receptors on the walls of blood vessels, including arteries, the level of binding of Lp(a) to the LDL receptors is reduced, thereby reducing the potentially deleterious effects of Lp(a) and, consequently, reducing the incidence of cardiovascular disorders that may be caused by high Lp(a) levels.

The magnesium arginate and zinc arginate of the EXEMPLARY COMPOSITION, which are forms of arginine, are known to relax blood vessels and thereby improve blood flow, thus reducing hypertension, or high blood pressure. The niacinamide of the EXEMPLARY COMPOSITION also improves blood flow, although not in as broad a fashion as arginine. Specifically, niacinamide is known to have a flushing affect on peripheral circulation (e.g., in the blood vessels at the surface of the skin). *Ginkgo Biloba* is also believed to open blood vessels and, thus, to improve blood flow.

Antioxidants that are included in the EXEMPLARY COMPOSITION include both hydrophilic and hydrophobic antioxidants, although compositions that include only hydrophilic or hydrophobic antioxidants are also within the scope of the invention. Vitamin E and beta-carotene, which are listed as components of the EXEMPLARY COMPOSITION, are examples of hydrophobic antioxidants. Vitamin E and beta-carotene are particularly useful in treating or preventing cardiovascular disease since they may be dissolved in fats, such as LDL cholesterol and Lp(a), and remain therein. Magnesium dehydroascorbic acid and ascorbic acid, both of which are forms of vitamin C, are examples of hydrophilic antioxidants that are included in the EXEMPLARY COMPOSITION. Another antioxidant that is included in the EXEMPLARY COMPOSITION, Coenzyme Q$_{10}$, or "CoQ$_{10}$," also acts as an electron-transport carrier. It is also believed that CoQ$_{10}$ provides nutrition at the cellular level and that CoQ$_{10}$ may increase blood flow, thereby reducing high blood pressure, or hypertension. Patients with cardiovascular disorders often exhibit CoQ$_{10}$ deficiency. In view of this knowledge, CoQ$_{10}$ has long been used in treating the lesions that occur in various cardiovascular disorders, as well as the causes of cardiovascular disorders (e.g., high blood pressure, inflammation, etc.).

Resveratrol, which is an extract of red wine and is also known as the "French Paradox," is known to keep fats from being oxidized and depositing in the arteries. Of course, the inclusion of other fat oxidation prevention elements in a composition that incorporates teachings of the present invention is also within the scope of the present invention.

Blood cholesterol reducers of the composition described in the EXEMPLARY COMPOSITION include niacinamide, which is also known in the art as "nicotinamide" and is a form of niacin, or Vitamin $B_3$. Specifically, niacinamide is known to lower LDL cholesterol, Lp(a), triglyceride, and fibrinogen levels while raising high-density lipoprotein (HDL) cholesterol (or "good cholesterol") levels.

The functions and effects (believed, theoretical, or actual) of each of the remaining components of the EXEMPLARY COMPOSITION on the cardiovascular health of a subject are well documented in the art.

Therapeutic methods which include use of a composition according to the present invention or combinations of the components thereof enlist the immune system of a treated subject to attack inflammation-causing pathogens, thereby reducing inflammation that may result in cardiovascular disorders. The immune system of a treated subject is enlisted by administering (e.g., enterally or parenterally) a composition which includes one or more types of transfer factor, as described previously herein, to a subject. The manner in which transfer factor initiates activity by various components of a subject's immune system is well known and documented in the art.

A therapy method incorporating teachings of the present invention may also include one or more of the following acts: preventing Lp(a) from binding to LDL receptors on the walls of blood vessels; preventing and/or repairing damage to the blood vessels (e.g., with an antioxidant or combination of antioxidants); reducing inflammation; improving blood flow; reducing blood cholesterol levels; and preventing fats from oxidizing and, thus, from sticking to the walls of blood vessels.

Examples of the possible benefits of therapy in accordance with teachings of the present invention follow:

Exemplary Benefits

A sixty-four (64) year old male who was suffering from low blood pressure (72 over 52) began taking the EXEMPLARY COMPOSITION, gradually increasing his dosage from two capsules daily to eight capsules per day. In addition, following the initial two capsule per day dosage, he began taking three capsules each of TRANSFER FACTOR™ and TRANSFER FACTOR PLUS™, both of which are available from 4Life Research, LLC, of Sandy, Utah, as well as four capsules of PBGS+®, also available from 4Life Research, each day. Within six months of initiating therapy, his blood pressure increased to normal levels (110 over 73).

A fifty-one (51) year old female who had been diagnosed with pulmonary fibrosis suffered from a resting heart rate of ninety-nine (99) beats per minute and high blood pressure (156 over 96), despite taking various medications which had been prescribed for her. Within fourteen days of taking three capsules of TRANSFER FACTOR™ and four capsules of the EXEMPLARY COMPOSITION each day, along with her normal medication, her resting heart rate decreased to sixty-nine (69) beats per minute and her blood pressure returned to normal levels (120 over 78).

A female who had three abnormal electrocardiograms within a three-month period received a normal electrocardiogram within two months of when she began taking four capsules of the EXEMPLARY COMPOSITION each day.

An eighty-nine (89) year old woman suffering from ischemic heart disease and congestive heart failure had symptoms of severe shortness of breath on mild exertion (walking for about five to about ten meters with support) and coughing. Initially, she was given two capsules of the EXEMPLARY COMPOSITION each day. Within three weeks, her breathing had improved somewhat. Further improvements were noted after five weeks of therapy. At two months, walking with support no longer resulted in shortness of breath. In addition, healthy increases in appetite and weight were noted.

A fifty-four (54) year old male suffering from angina had three coronary arteries that were occluded by about 75% to about 80%. He began therapy with four capsules of the EXEMPLARY COMPOSITION twice daily (i.e., eight capsules per day), along with three capsules of TRANSFER FACTOR™ each day. Within four months, the occlusion or blockage of the same three arteries had reduced to about 30% to about 40%.

A forty-nine (49) year old male suffering from Grave's disease and high blood pressure no longer suffered any physical problems within three months of beginning four capsule per day therapy with the EXEMPLARY COMPOSITION.

Another sixty-four (64) year old male who had been diagnosed with cardiomyopathy was suffering symptoms including lack of both energy and stamina and shortness of breath. Almost immediately following the initiation of four capsule per day therapy with the EXEMPLARY COMPOSITION, these symptoms began to subside. Shortly after increasing his daily dosage to eight capsules per day, the subject no longer had any cardiomyopathy-related symptoms.

A male who had tested at a 7.93 for C-reactive proteins (CRPs), which are indicative of risk for heart attack and measured on a scale of 1.0 to 8.7, began taking, on the day of receiving his CRP results, four capsules of the EXEMPLARY COMPOSITION and three capsules of TRANSFER FACTOR™ daily. Within four months, his CRP levels were reduced to 1.1.

A thirty-two (32) year old male who takes four capsules of the EXEMPLARY COMPOSITION each day and, prior to taking the EXEMPLARY COMPOSITION, had long maintained a consistent exercise regimen, began recognizing less shortness of breath from aerobic activity and less joint pain within two months of initiating therapy with the EXEMPLARY COMPOSITION.

A male with chronic pain in his knees no longer had pain within two weeks of taking four capsules of the EXEMPLARY COMPOSITION and three capsules of TRANSFER FACTOR™ each day.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Moreover, features from different embodiments of the invention may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed:
1. A nutritional supplement, comprising:
at least one vitamin;
at least one mineral;

at least one herb or plant extract selected from the group comprising Butcher's Broom, Ginkgo biloba, hawthorn, garlic, red rice yeast extract, resveratrol and ginger; and a cardiovascular support component, consisting of:
an inflamation-reducing component for decreasing an amount of inflammation in blood vessels of a subject, comprising transfer factor;
at least one low density lipoprotein (LDL) receptor-binding component;
at least one blood cholesterol reduction component;
at least one blood flow-enhancing component; and
at least one antioxidant.

2. The nutritional supplement of claim 1, wherein the transfer factor is at least one of an extract from a mammalian source and an extract from a nonmammalian source.

3. The nutritional supplement of claim 1, wherein the at least one low density lipoprotein (LDL) receptor-binding component is lysine or a lysine salt.

4. The nutritional supplement of claim 1, wherein the at least one blood flow-enhancing component is at least one of an arginine-containing compound and niacinamide.

5. The nutritional supplement of claim 1, wherein the at least one antioxidant is a hydrophobic antioxidant.

6. The nutritional supplement of claim 5, wherein the hydrophobic antioxidant is at least one of beta-carotene, vitamin A, and vitamin E.

7. The nutritional supplement of claim 1, wherein the at least one antioxidant is Coenzyme $Q_{10}$.

8. The nutritional supplement of claim 1, wherein the at least one herb or plant extract is a fat oxidation prevention element.

9. A nutritional supplement, comprising:
at least one vitamin;
at least one antioxidant;
at least one mineral;
at least one herb or plant extract selected from the group comprising Butcher's Broom, Ginkgo biloba, hawthorn, garlic, red rice yeast extract, resveratrol and ginger; and
a cardiovascular support component, consisting of:
a pathogen-reducing component for decreasing a number of pathogens in blood vessels of a subject, comprising transfer factor; and
at least one blood flow-enhancing component.

10. The nutritional supplement of claim 9, wherein the transfer factor is at least one of an extract from a mammalian source and an extract from a nonmammalian source.

11. The nutritional supplement of claim 9, wherein the at least one mineral is part of an LDL receptor-binding component.

12. The nutritional supplement of claim 11, wherein the LDL receptor-binding component is a lysine salt of the at least one mineral.

13. The nutritional supplement of claim 9, wherein the at least one blood flow-enhancing component is at least one of an arginine-containing compound and niacinamide.

14. The nutritional supplement of claim 9, wherein at least one vitamin, at least one mineral, or at least one herb is the at least one antioxidant.

15. The nutritional supplement of claim 14, wherein the at least one antioxidant is a hydrophobic antioxidant.

16. The nutritional supplement of claim 15, wherein the at least one antioxidant is at least one of beta-carotene, vitamin A, and vitamin E.

17. The nutritional supplement of claim 9, wherein the at least one antioxidant is Coenzyme $Q_{10}$.

18. The nutritional supplement of claim 9, wherein the at least one vitamin is a cholesterol-reducing element.

19. The nutritional supplement of claim 9, wherein the at least one herb or plant extract is a fat oxidation prevention element.

20. A nutritional supplement, comprising:
at least one vitamin;
at least one antioxidant;
at least one mineral;
at least one herb or plant extract selected from the group comprising Butcher's Broom, Ginkgo biloba, hawthorn, garlic, red rice yeast extract, resveratrol and ginger; and
a cardiovascular support component, consisting of:
an avian transfer factor preparation;
Vitamin C;
niacinamide;
an arginine-containing compound; and
a lysine-containing compound.

21. The composition of claim 20, wherein:
the arginine-containing compound comprises magnesium arginate; and
the lysine-containing compound comprises magnesium lysinate.

22. The composition of claim 20, comprising the preparation including transfer factor and the Vitamin C in substantially equal amounts.

23. The composition of claim 20, wherein the avian transfer factor preparation is specific for at least one pathogen that directly causes a cardiovascular disorder or at least one antigen of at least one pathogen that directly causes the cardiovascular disorder.

24. A composition, comprising a preparation including transfer factor and Vitamin C, the preparation including transfer factor and the Vitamin C included in the composition in substantially equal amounts.

25. The composition of claim 24, wherein the transfer factor is specific for at least one of herpes simplex virus-1, herpes simplex virus-2, cytomegalovirus, *Chlamydia pneumoniae*, and *Helicobacter pylori*.

26. The composition of claim 1, wherein the transfer factor is an antigen-nonspecific transfer factor or a pathogen-nonspecific transfer factor.

27. The composition of claim 1, wherein the transfer factor is a combination of nonspecific transfer factor and specific transfer factor.

28. The composition of claim 1, wherein the transfer factor is an antigen-specific transfer factor or a pathogen-specific transfer factor.

29. The composition of claim 28, wherein the transfer factor is specific for pathogenic agents that affect the circulatory system.

30. The composition of claim 29, wherein the transfer factor is specific for pathogenic agents that cause cardiovascular complications.

31. The composition of claim 30, wherein the transfer factor is specific for pathogenic agents that cause arterial walls to swell.

32. The composition of claim 1, wherein the transfer factor is specific for at least one of cytomegalovirus, *Chlamydia pneumoniae*, and *Helicobacter pylori*.

33. The composition of claim 9, wherein the pathogen-reducing component is a transfer factor-containing extract.

34. The composition of claim 33, wherein transfer factor of the transfer factor-containing extract is specific for at least one of cytomegalovirus, *Chlamydia pneumoniae*, and *Helicobacter pylori*.

35. The composition of claim 20, wherein transfer factor of the avian transfer factor preparation is specific for at least one of cytomegalovirus, *Chlamydia pneumoniae*, and *Helicobacter pylori*.

* * * * *